US00PP33539P2

(12) United States Plant Patent
Hanes

(10) Patent No.: US PP33,539 P2
(45) Date of Patent: Oct. 5, 2021

(54) ***CALIBRACHOA* PLANT NAMED 'CBRZ0038'**

(50) Latin Name: *Calibrachoa hybrida*
Varietal Denomination: CBRZ0038

(71) Applicant: SYNGENTA CROP PROTECTION AG, Basel (CH)

(72) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/079,563

(22) Filed: Oct. 26, 2020

(51) Int. Cl.
*A01H 6/82* (2018.01)
*A01H 5/02* (2018.01)

(52) U.S. Cl.
USPC ..... Plt./413

(58) Field of Classification Search
USPC ..... Plt./413
See application file for complete search history.

*Primary Examiner* — Annette H Para
(74) *Attorney, Agent, or Firm* — Dale Skalla

(57) ABSTRACT

A new *Calibrachoa* plant named 'CBRZ0038' particularly distinguished by mid-sized purple blue flowers with a darker "eye" and yellow inside the flower at the base of the petals, mid-green foliage, good branching, early flowering, semi-trailing plant habit, and has little sensitivity to soil pH.

1 Drawing Sheet

Latin name of the genus and species of the plant claimed: *Calibrachoa hybrida.*

Varietal denomination: 'CBRZ0038'.

BACKGROUND OF THE NEW PLANT

The present invention comprises a new *Calibrachoa*, botanically known as *Calibrachoa hybrida*, and hereinafter referred to by the variety name 'CBRZ0038'.

'CBRZ0038' is a product of a planned breeding program. The new cultivar has mid-sized purple blue flowers with a darker "eye" and yellow inside the flower at the base of the petals, mid-green foliage, good branching, early flowering, semi-trailing plant habit, and has little sensitivity to soil pH.

'CBRZ0038' originated from a hybridization made in July 2014 in a greenhouse in Gilroy, Calif. The female parent was an unpatented non-commercial variety '4132-4' with a raspberry and dark eyed flower on a trailing plant.

The male parent of 'CBRZ0038' was an unpatented proprietary plant known as '4151-1' having rose with yellow center flowers, moderately upright plant, originating from a seedling selected in Gilroy, Calif.

The resulting seeds were sown in August 2015 and 'CBRZ0038' was selected as one flowering plant within the progeny of the stated cross in December 2015 in a controlled environment in Gilroy, Calif.

The first act of asexual reproduction of 'CBRZ0038' was accomplished when vegetative stem cuttings were propagated from the initial selection in January 2016 in a controlled environment in Gilroy, Calif.

BRIEF SUMMARY OF INVENTION

Horticultural examination of plants grown from cuttings of the plant initiated in the spring of 2016, and continuing thereafter, has demonstrated that the combination of characteristics as herein disclosed for 'CBRZ0038' are firmly fixed and are retained through successive generations of asexual reproduction.

'CBRZ0038' has not been observed under all possible environmental conditions. The phenotype may vary significantly with variations in environment such as temperature, light intensity, and day length.

A Plant Breeder's Right for this cultivar has not yet been applied for. 'CBRZ0038' has not been made publicly available prior to the effective filing date of this application, notwithstanding any disclosure that may have been made less than one year prior to the effective filing date of this application by the inventor or another who obtained 'CBRZ0038' directly from the inventor.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

Figure 1:
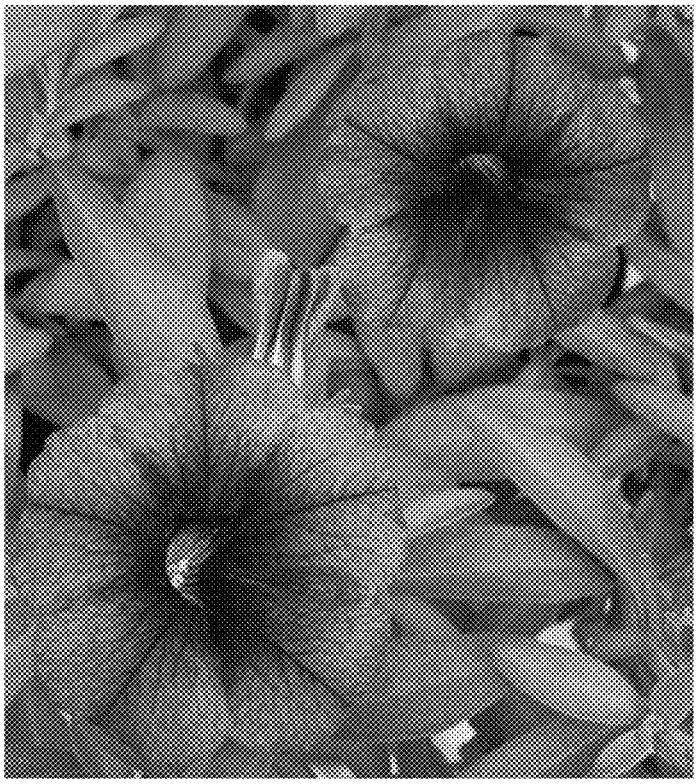
Figure 2:
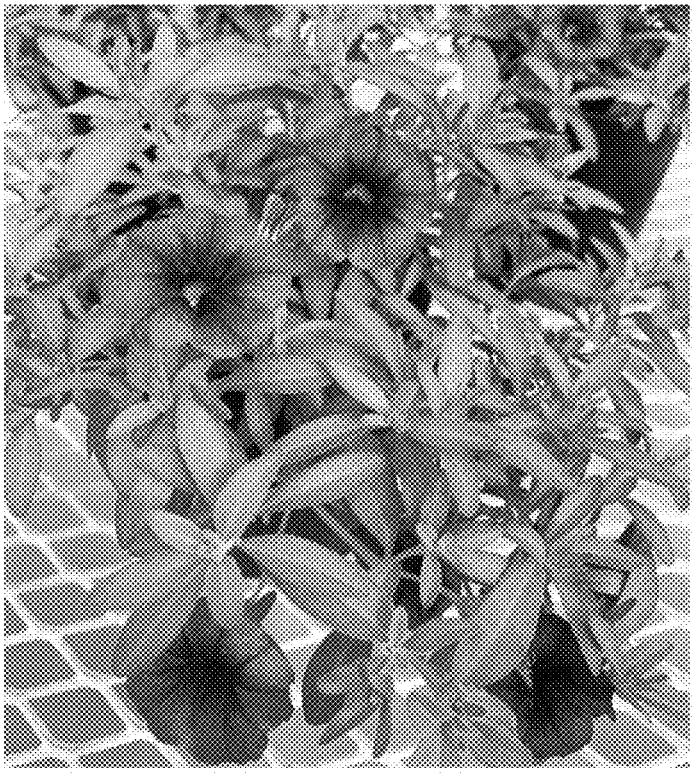

The accompanying photographic drawing shows typical flower and foliage characteristics of 'CBRZ0038' with colors being as true as possible with an illustration of this type. The photographic drawings show in FIG. 1 a close-up of the flowers and in FIG. 2 a flowering plant of the new variety.

DETAILED BOTANICAL DESCRIPTION

The aforementioned photographs were taken in September 2020 in a greenhouse in Gilroy, Calif.

The measurements and observations were made in October 2020 in Gilroy, Calif. on plants grown in 4 inch pots in the greenhouse.

Color references are made to The Royal Horticultural Society Colour Chart (R.H.S.) 2015.

TABLE 1

DIFFERENCES BETWEEN THE NEW VARIETY 'CBRZ0038' AND A SIMILAR VARIETY

| | 'CBRZ0038' | 'CBRZ0011', U.S. Plant Pat. No. 29,953 |
|---|---|---|
| Leaves: | Mid-green | Green |
| Earliness to flower: | Early | Late |
| Plant habit as a young plant: | Basal branching | Semi upright then trailing |

Plant:

*Form, growth and habit.*—Moderately compact and mounding, very well branched.

*Plant height.*—12 cm.

*Plant height (inflorescence included).*—12 cm.

*Plant width.*—30 cm.

*Quantity of main branches.*—16-20.

*Quantity of secondary branches.*—4-6 per basal branch.

*Time to produce a flowering plant.*—7-8 weeks for a 12 cm pot (from planting of rooted cuttings).

Roots:

*Number of days to initiate.*—18-21 days at about 22° C.

*Number of days to produce a rooted cutting.*—21-24 days at 22° C.

*Type.*—Fibrous.

*Color.*—RHS 158D.

Stem:

*Color of stem.*—Mainly RHS 146B.

*Length of stem.*—Approximately 7-11 cm.

*Diameter.*—0.2 cm.

*Length of internodes.*—1.7-2.0 cm.

*Texture.*—Smooth, hairless.

Foliage:

*Immature leaf, color of upper surface.*—RHS 146A.

*Immature leaf, color of lower surface.*—RHS 146B.

*Mature leaf, color of upper surface.*—RHS 146A.

*Mature leaf, color of lower surface.*—RHS 146B.

*Leaf blade, length.*—3.0 cm.

*Leaf, width.*—1.1 cm.

*Shape.*—Elliptical, narrow.

*Base shape.*—Acuminate.

*Apex shape.*—Obtuse.

*Margin.*—Entire.

*Texture.*—Hairless.

*Color of veins, upper surface.*—RHS 146A.

*Color of veins lower surface.*—RHS 146C.

*Petiole color.*—RHS 146B.

*Petiole length.*—0.1-0.3 cm.

*Diameter of petiole.*—0.1 cm.

*Texture.*—Smooth.

Inflorescence:

*Type.*—Flowers solitary in upper leaf axis and slanting upright or outwards.

*Quantity of inflorescences per plant.*—Approximately 40.

*Lastingness of individual flowers.*—About 7-9 days.

*Fragrance.*—None.

*Duration of flowering.*—Continuous flowering throughout the summer.

Pedicel:

*Color of pedicel.*—RHS 146B.

*Length of pedicel.*—2.5-2.8 cm.

*Diameter of pedicel.*—1.0 mm.

*Texture of pedicel.*—Smooth, hairless.

Flower:

*Immature flowers, corolla upper surface.*—RHS 79A.

*Immature flowers, corolla lower surface.*—RHS 150C/D.

*Mature flowers, color upper surface.*—RHS N81A with a somewhat deeper, purple ring, RHS 83A in the center around the throat opening. Deep in throat is a yellow color RHS 151C.

*Mature flowers, color lower surface.*—RHS 77B.

*Flower horizontal diameter.*—3.3 cm.

*Flower height (vertical).*—0.9-1.0 cm.

*Corolla tube length.*—About 1.1 cm.

*Petal apex shape.*—Truncate.

*Margin.*—Entire.

*Waviness of petals.*—Weak.

*Petal lobation.*—Moderate.

*Corolla texture.*—Smooth.

*Corolla tube color inside.*—RHS 151C.

*Corolla tube color outside.*—RHS 149C.

Bud (just before opening):

*Color at apex.*—RHS 79A.

*Length.*—2.5 cm.

*Width (upper end).*—1.0 cm.

*Shape.*—Oblong.

Calyx:

*Number of sepals.*—5.

*Color of sepals, adaxial or upper surface.*—RHS 144A.

*Color of sepals, abaxial or lower surface.*—RHS 144A.

*Length of sepals.*—14-16 mm.

*Width of sepals.*—3 mm.

*Sepal shape.*—Lanceolate.

*Apex shape.*—Acute.

*Margins.*—Entire.

*Texture.*—Smooth.

Reproductive organs:

*Pistil.*—1.

*Length.*—1.3 cm.

*Style color.*—RHS 145B.

*Style length.*—0.8-0.9 cm.

*Stigma color.*—RHS 144B.

*Number of stamens.*—5.

*Color of filaments.*—RHS 4D.

*Length filaments.*—0.7-1.1 cm.

*Color of pollen.*—RHS 13C.

*Pollen amount.*—Moderate.

*Fertility/seed set.*—Not observed on this hybrid.

*Disease/pest resistance.*—Not observed on this hybrid.

What is claimed is:

1. A new and distinct variety of *Calibrachoa* plant named 'CBRZ0038', substantially as illustrated and described herein.

* * * * *